United States Patent
Carlson et al.

(10) Patent No.: US 6,363,787 B1
(45) Date of Patent: Apr. 2, 2002

(54) APPARATUS AND METHOD FOR MEASURING THE THICKNESS OF A COATING

(75) Inventors: Nancy M. Carlson; John A. Johnson; David M. Tow; John B Walter, all of Idaho Falls, ID (US)

(73) Assignee: Bechtel BWXT Idaho LLC, Idaho Falls, ID (US)

( * ) Notice: Subject to any disclaimer, the term of this patent is extended or adjusted under 35 U.S.C. 154(b) by 0 days.

(21) Appl. No.: 09/460,041

(22) Filed: Dec. 13, 1999

(51) Int. Cl.[7] .............................................. G01N 29/08
(52) U.S. Cl. .............................. 73/579; 73/597; 73/598; 73/599; 73/643
(58) Field of Search ......................... 73/579, 597, 598, 73/599, 600, 602, 624, 625, 627, 643; 310/313 R

(56) References Cited

U.S. PATENT DOCUMENTS

| | | | | |
|---|---|---|---|---|
| 4,539,847 A | * | 9/1985 | Paap | 73/579 |
| 5,035,144 A | * | 7/1991 | Aussel | 73/602 |
| 5,038,615 A | * | 8/1991 | Trulson et al. | 73/597 |
| 5,305,239 A | * | 4/1994 | Kinra | 73/602 |
| 5,358,753 A | * | 10/1994 | Rao et al. | 427/451 |
| 5,681,996 A | * | 10/1997 | White | 73/622 |
| 5,767,408 A | * | 6/1998 | Lindgren et al. | 73/597 |
| 5,894,092 A | * | 4/1999 | Lindgren et al. | 73/598 |
| 5,965,818 A | * | 10/1999 | Wang | 763/598 |
| 6,127,768 A | * | 10/2000 | Stoner et al. | 310/313 |

OTHER PUBLICATIONS

Lakestani, F., et al., "Application of ultrasonic Rayleigh waves to thickness measurement of mettalic coatings", *NDT & E International*, vol. 28, No. 3, pp. 171 178 (1995).
Lorenz, M., et al., "Opto–Acoustical Inspection of Surface Layers", *Nondestr. Test. Eval.* vol. 5, pp. 187–202.
Neubrand, A., et al., "Laser generation and detection of surface acoustic waves: elastic properties fo surface layers", *J. Appl. Phys.* 71 (1), pp. 227–238.

\* cited by examiner

*Primary Examiner*—Hezron Williams
*Assistant Examiner*—Jacques M Saint-Surin
(74) *Attorney, Agent, or Firm*—Klaas Law O'Meara & Malkin

(57) ABSTRACT

An apparatus and method for measuring the thickness of a coating adhered to a substrate. An electromagnetic acoustic transducer is used to induce surface waves into the coating. The surface waves have a selected frequency and a fixed wavelength. Interpolation is used to determine the frequency of surface waves that propagate through the coating with the least attenuation. The phase velocity of the surface waves having this frequency is then calculated. The phase velocity is compared to known phase velocity/thickness tables to determine the thickness of the coating.

27 Claims, 9 Drawing Sheets

APPARATUS AND METHOD FOR MEASURING THE THICKNESS OF A COATING

CONTRACTUAL ORIGIN OF THE INVENTION

The United States Government has rights in this invention pursuant to Contract No. DE-AC07-94ID13223 between the United States Department of Energy and Lockheed Martin Idaho Technologies Company, now Contract No. DE-AC07-99ID13727 with Bechtel BWXT Idaho, LLC.

TECHNICAL FIELD OF THE INVENTION

The present invention generally relates to measuring the thickness of a coating adhered to a substrate and, more particularly, to measuring the thickness of a coating adhered to a substrate by measuring the phase velocity of surface waves propagating through the coating and the substrate and correlating the phase velocity to the thickness of the coating.

BACKGROUND OF THE INVENTION

In an effort to produce more efficient and economical products, many industries have been producing products by combining various materials in order to gain the benefits of the individual materials. These materials alone typically are not suited for the products, however, when the materials are combined, they offer many benefits over traditional materials. For example, some industries have the need for lighter products that have the integrity of conventional heavier products. Manufacturers produce these lighter products with a substantial proportion of lighter materials and combine the lighter materials with a limited amount of another material that improves the integrity of the lighter material. Thus, the final product is lightweight and has a high degree of integrity. For example, the product may be substantially comprised of a light material, such as aluminum, and may be coated with a limited quantity of a more durable material, such as steel. Accordingly, the final product is lightweight, similar to an aluminum product, and it has the integrity of a product made of steel. In most applications, only a few mils of steel coating is required to substantially improve the integrity of the aluminum product.

One example of the use of coated materials is in the automotive industry. In order to produce more efficient motorized vehicles, some manufacturers are fabricating internal combustion engine blocks from aluminum rather than from more traditional metals such as cast iron. Aluminum is relatively lightweight and aluminum products are relatively easily fabricated, which decreases the weight and manufacturing cost of the engine block and, accordingly, the motorized vehicle. Aluminum, however, is relatively soft and is generally not able to withstand the forces and extreme conditions present in an internal combustion engine. For example, the cylinder walls in the engine block are subject to extreme heat when the fuel is burned and friction as the pistons travel the lengths of the cylinder walls. These conditions on the cylinder walls of an aluminum engine block will cause the engine block to wear and fail after a relatively short period of service.

In order to increase the integrity of the cylinder walls in the aluminum engine block, the cylinder walls are typically coated with a hard material. For example, the cylinder walls may have steel applied to them via a plasma spray. The steel coating increases the durability of the cylinder walls, which in turn, increases the period of service of the aluminum engine block. It has been found that a steel coating of only a few mils will substantially increase the durability of the cylinder walls.

The internal combustion engine, however, will encounter problems if the coating is too thick or too thin. If the coating is too thick, it may impede the movement of the pistons in the cylinders. The impeded movement of the pistons may cause the pistons to score the walls of the cylinder or create excessive heat within the engine, either of which will cause the premature failure of the engine. Furthermore, the application of the plasma coating is expensive and time consuming. Thus, if the coating is thicker than necessary for the operation of the engine, the cost of producing the engine and, thus, the motorized vehicle will increase accordingly.

If, on the other hand, the coating is too thin, friction created by the moving pistons may wear the coating from the cylinder walls and expose the underlying aluminum to the moving pistons. This defeats the purpose of coating the block because the aluminum cylinder walls will directly contact the pistons. As previously set forth, the aluminum alone is soft, thus, the pistons will rapidly wear the aluminum cylinders, which will cause the engine to fail prematurely. In addition, if the coating on one portion of a cylinder wall is very thin, another portion of the cylinder wall may have no coating, which will lead to the rapid failure of the engine.

Further problems will be encountered if the coating is not evenly applied to the cylinder walls. For example, if one side of a cylinder has a thicker coating than the opposite side, the cross-sectional shape of the cylinder will be oblong instead of round. The aforementioned problems will likely be encountered wherein the thickly coated areas of the cylinder walls will impede the movement of the pistons and the thinly coated areas of the cylinder walls will wear prematurely. Either of these problems will cause the premature failure of the engine.

Per the above description, it is crucial that engines are not manufactured from blocks that are improperly coated. Accordingly, the coating thickness and uniformity must be accurately measured so defective blocks are identified and not used in the production of engines. Measuring the coating thickness in a product such as an engine block, however, poses several obstacles, some of which are described below. One example of an obstacle is that the coating thickness must be measured quickly and accurately in a manufacturing environment. If an extended period is required to measure the coating thickness, the price of the engine will increase to reflect the extended measuring period. Another example of an obstacle is that the measuring method must yield results that are easily interpreted by an operator. If the results are difficult to interpret, the operator of the measuring system may indicate that improperly coated blocks have been properly coated, which will result in these defective blocks being used in engines. Yet another example of an obstacle is that the testing must be nondestructive. Destructive testing destroys a portion of the block, which typically increases the cost of the engine and decreases the service period of the engine.

Several methods of measuring the thickness of coatings are presently used in the art; however, they all have drawbacks when they are used to measure a coating adhered to the concave geometry inherent on the surface of a cylinder wall. One method of measuring the thickness of a coating is known in the art as the "thermal wave method." Using this approach, a predetermined portion of the coating is heated. Thermal sensors monitor the heat transmission through the coating and, based on the measured heat transmission, the thickness of the coating may be determined. The equipment required for the thermal wave method is relatively expensive and difficult to use, especially within the confines of a cylinder. Thus, the thermal wave method of measuring the thickness of a coating is not readily applicable for use in the automotive industry.

Another method of measuring the thickness of a coating is achieved by measuring Eddy currents as is known in the art. Using the Eddy current method provides a sensitive measuring technique, however, the Eddy currents may indicate that variations in the coating thickness exist, when in reality, variations in the microstructure of the coating exist. Thus, the Eddy current method may provide confusing information for an operator and, accordingly, is not readily applicable for use on a production line in the automotive industry.

Another method of measuring the thickness of a coating involves using beta particles emitted by radioactive isotopes. This method, however, may pose health risks to the technicians performing the measurements. Accordingly, this method is not preferred for use on a production line.

Therefore, a measuring device and technique are needed that will measure the thickness of a coating adhered to a curved surface, wherein the measuring device and technique are relatively easy to use and are applicable for use in an automotive manufacturing environment.

SUMMARY OF THE INVENTION

An apparatus and method for measuring the thickness of a coating adhered to a substrate are disclosed herein. The combination of the coating and the substrate is sometimes referred to herein as the coated material. The apparatus and method are based on principles of surface waves wherein the phase velocity of a surface wave propagating in a coated material is dependent on the thickness of the coating. The apparatus and method are also based on principles of surface waves wherein the coating functions as a bandpass filter for surface waves and wherein a specific frequency of a surface wave undergoes minimal attenuation as it propagates in the coated material. The apparatus and method disclosed herein induce surface waves having fixed and predetermined wavelengths and frequencies into the coated material. Interpolation is used to determine the frequency of surface waves that propagate in the coated material with minimal attenuation. Because the surface waves have a fixed wavelength, the phase velocity of these surface waves is readily determined. This phase velocity is then correlated to a coating thickness.

The measurement apparatus comprises a transmitter, a receiver, and a processor. The transmitter may be of a type known as an "electromagnetic acoustic transducer" (EMAT) and serves to induce surface waves into the coated material. The receiver may also be an EMAT that is substantially identical to the transmitter and serves to generate an electric waveform that is representative of the surface waves that propagate in the coated material. The processor is electrically connected to both the transmitter and the receiver. The processor serves to instruct the transmitter as to the frequency of surface waves to induce into the coated material. The processor further serves to analyze the waveform generated by the receiver.

During the measurement process, the processor instructs the transmitter to induce a selected frequency of surface waves into the coated material. The surface waves, accordingly, propagate through the coated material. The receiver, via the EMAT, detects the surface waves after they have propagated through the coated material and generates an electrical representation of the surface waves. The electrical representation of the surface waves is transmitted to the processor for analysis.

The processor analyzes the waveform generated by the receiver to determine the frequency of the surface waves that propagate through the coated material with minimal attenuation. This is accomplished by obtaining the frequency spectrum of the waveform and determining the maximum amplitude of the frequency spectrum and the frequency of the maximum amplitude. The process of inducing surface waves and analyzing the waveform generated by the receiver is repeated for a plurality of frequencies. When a plurality of waveforms generated by the receiver have been analyzed, the processor fits a quadratic equation to the maximum amplitudes based on their corresponding frequencies. The processor then determines the maximum value of the quadratic equation and its corresponding frequency, denoted as $f_p$. The frequency $f_p$ is the frequency of surface waves that propagate in the coated material with the least attenuation. Based on the frequency $f_p$, the processor determines the phase velocity of the surface waves having this frequency and correlates this phase velocity to a thickness of the coating.

DETAILED DESCRIPTION OF A PREFERRED EMBODIMENT

Figure 1:
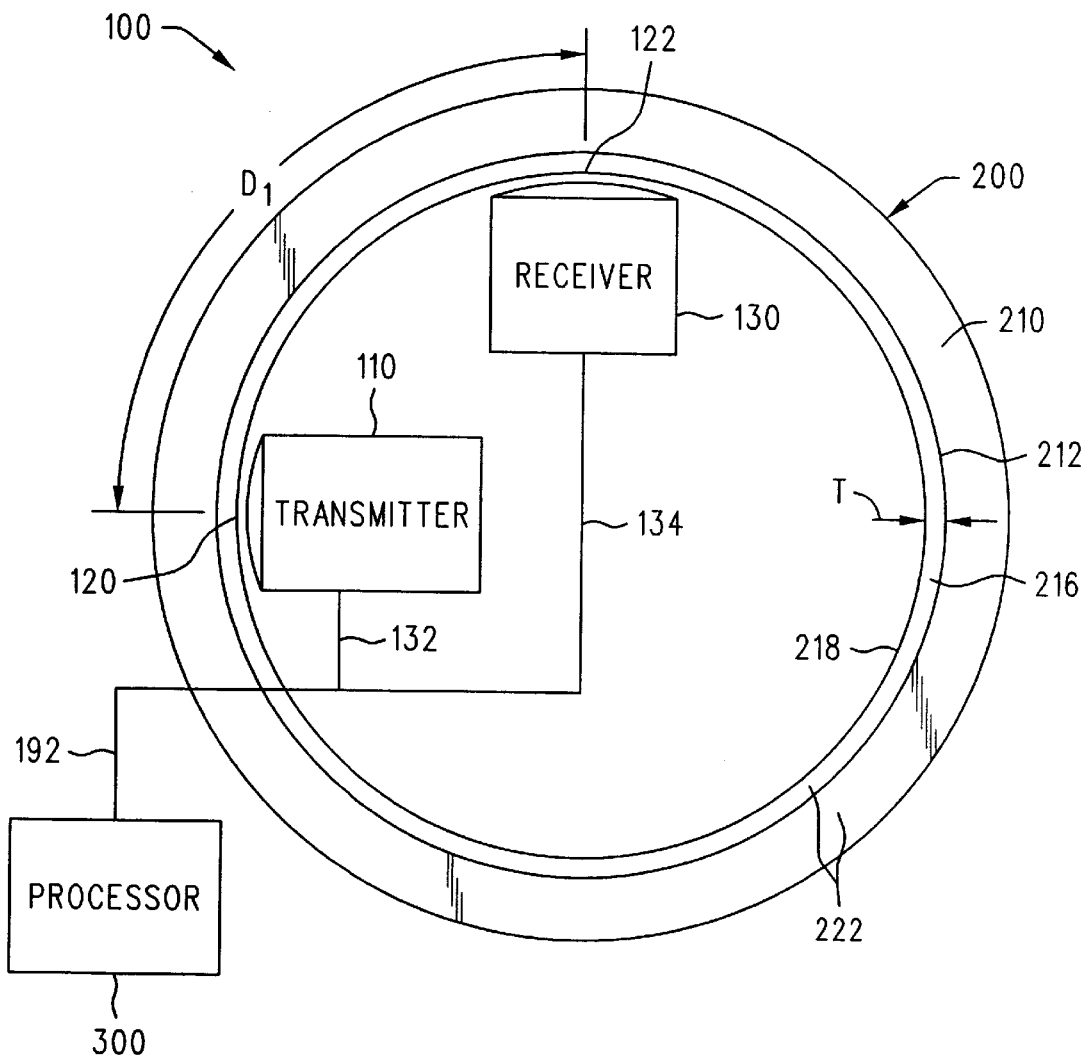
FIG. 1 is a top view of a measurement system positioned to measure the thickness of a coating applied to a cylinder wall.

A measuring system 100 and method for measuring the thickness of a coating adhered to a substrate are disclosed herein. Referring to FIG. 1, the following description focuses on measuring a thickness T of a coating 216 applied to a surface 212 of a substrate 210. In a preferred and non-limiting embodiment, the substrate 210 is an aluminum block of an internal combustion engine with the coating 216 being comprised of carbon steel. Accordingly, the substrate 210 is aluminum and the coating material 216 is carbon steel. The combination of the substrate 210 and the coating 216 is referred to herein as the coated material 222. It shall be understood that the apparatus and method disclosed herein may be adapted to measure the thicknesses of other coating materials adhered to other substrate materials without limitation. The following description includes a summary of the measuring system 100 followed by a more detailed description of the measuring system 100 and method for measuring the thickness of a coating adhered to a substrate.

One of the properties of a coated material is that the phase velocity of surface waves propagating through the coated material is dependent on the frequency of the surface waves and the thickness of the coating. Lower frequencies and thinner coatings tend to facilitate higher phase velocities. Another property of a coated material is that it functions similar to a band-pass filter wherein at a fixed wavelength, only a specific frequency of surface waves propagates through the coated material with minimal attenuation. This specific frequency is dependent on the thickness of the coating. These properties are used by the measuring system 100 to determine the thickness of coatings adhered to substrates. More specifically, the measuring system 100 determines the frequency of the surface waves that propagate in the coated material 222 with the least attenuation. This frequency is correlated to a phase velocity, which in turn, is correlated to a thickness T of the coating 216.

SUMMARY OF THE PREFERRED EMBODIMENTS

With reference to FIG. 1, in summary, a transmitter 110 induces surface waves (sometimes referred to as acoustic waves, Rayleigh waves or Love waves) into the coated material 222 via the coating 216. The induced surface waves have predetermined frequencies and a fixed wavelength. The frequency and wavelengths of the induced surface waves depend on the materials comprising the substrate 210 and the coating 216. A receiver 130 detects the surface waves as they propagate through the coated material 222 and generates an electronic representation of the surface waves, which is transmitted to a processor 300. The processor 300 calculates the phase velocity of the surface waves propagating in the coated material 222 and, based on the phase velocity, determines the thickness T of the coating 216.

Three embodiments of measuring systems and methods that use the above-described properties of wave propagation through coated materials are disclosed herein to measure the thickness of a coating adhered to a substrate. In summary, the first embodiment uses the transmitter 110 to induce bursts of acoustic surface waves into the coated material 222 via the coating 216. Each burst of surface waves has a predetermined frequency and all the bursts have the same fixed wavelength. The predetermined frequency induced into the coated material 222 is sometimes referred to as a "driving frequency."

Each burst of surface waves propagates through the coated material 222 and, due to the filtering properties of the coated material 222, creates narrow frequency bands of acoustic waves that propagate through the coated material 222. The receiver 130 is positioned in the proximity of the coating 216 and generates an electrical representation of each burst of surface waves after they have propagated through the coated material 222. A processor 300 performs a fast Fourier transform on the electrical representation of the surface waves to yield the frequency spectrum of each burst of surface waves. Based on the frequency spectrums, the processor 300 determines the frequency of the surface waves that propagate through the coated material 222 with the least attenuation. The phase velocity of surface waves having this frequency is readily calculated, which is then correlated to a thickness T of the coating 216.

Another embodiment uses the same arrangement of components employed in the measuring system 100 described above, however, the measurement procedure is different. In this embodiment, the approximate thickness T of the coating 216 is known, so a driving frequency can be selected that undergoes minimal attenuation, but not the minimum attenuation as it propagates through the coated material 222. In this embodiment, the driving frequencies induced into the coated material 222 by the transmitter 110 have a broad bandwidth with significant amplitude over the entire frequency range of interest. The amplitude and frequency band is dependent on the specific application. Only a narrow band of frequencies, however, centered about a single frequency will be propagated by the coated material 222 and received by the receiver 130. The received signal is processed by the processor 300 to determine the frequency that is minimally attenuated as it propagates in the coated material 222. The phase velocity of this frequency is readily calculated and the thickness T is then determined as described above by correlating the phase velocity of the surface waves to the thickness T.

The third embodiment of the measuring system 100 involves directly measuring the phase velocity of surface waves that propagate through the coated material 222. In this embodiment, surface waves having a fixed wavelength and predetermined frequency are induced into the coated material 222 by the transmitter 110 at a specific time. The receiver 130 is located at a predetermined distance D1 from the location where the surface waves are induced into the coated material 222 and monitors the coating 216 for surface waves. The phase velocity of the surface waves is readily determined by dividing the distance D1 by the time the surface waves take to propagate the distance D1. This phase velocity is then correlated to known velocity/thickness tables to determine the thickness T of the coating 216.

DETAILED DESCRIPTION OF THE PREFERRED EMBODIMENTS

Having generally described various embodiments of the measuring system 100 and a method for measuring the thickness of a coating, the measuring system 100 and corresponding method will now be described in even greater detail. The measuring system 100 is described herein, in a non-limiting fashion, measuring the thickness T of the coating 216 applied to the surface 212 of the cylinder 200. The cylinder 200 is bored into an aluminum engine block, not shown. The following description of the measuring system 100 measuring the thickness T of the coating 216 in the cylinder 200 is for illustration purposes only. It is to be understood that the measuring system 100 and method described herein may be used in other applications.

The measuring system 100 illustrated in FIG. 1 is positioned so as to measure the thickness T of the coating 216. The coating 216 is schematically shown as being adhered to a surface 212 of a cylinder 200. The cylinder 200 is comprised of the substrate 210 and the coating 216 adhered thereto, wherein the substrate 210 is the aluminum engine block. The coating 216 is preferably made from carbon steel (sometimes referred to herein simply as steel). The combination of the substrate 210 and the coating 216 is again referred to herein as the coated material 222. It is to be understood, however, that the use of the aluminum engine block and the steel coating are for illustration purposes only and that the measuring system 100 and method disclosed herein may be applicable to measuring the thicknesses of coating materials other than steel and adhered to substrate materials other than aluminum.

With reference to FIG. 1, the coating 216 has an inner surface 218 that faces into the cylinder 200. The coating thickness T extends between the surface 212 of the cylinder 200 and the inner surface 218. The coating 216 may, for example, be applied to the surface 212 by a plasma spray as is known in the art and typically has a thickness T of about two to eight mils. For illustration purposes, the thickness T of the coating 216 shown in FIG. I has been greatly enlarged.

The measuring system 100 has a transmitter 110, a receiver 130, and a processor 300. The transmitter 110 and receiver 130 are sometimes referred to herein as the first transducer and the second transducer respectively. The transmitter 110 and receiver 130 are illustrated herein as being electromagnetic acoustic transducers (sometimes referred to herein simply as EMATs) as are known in the art. The transmitter 110 is electrically connected to the processor 300 by a data line 132 and a wiring harness 192. The processor 300 is described in detail below. The receiver 130 is electrically connected to the processor 300 by a data line 134 and the wiring harness 192.

When the measuring system 100 is in use, the transmitter 110 is positioned adjacent a transmission point 120 on the inner surface 218 of the coating 216. Likewise, the receiver 130 is positioned adjacent a receiving point 122 on the inner surface 218. The transmission point 120 and the receiving point 122 are separated by an arcuate distance D1 wherein the distance D1 is measured along the curved inner surface 218. The transmission point 120 and the receiving point 122 are illustrated in FIG. 1 as being points on the inner surface 218 of the coating 216 due to the cross-sectional view of FIG. 1. As will be described below, they, in reality, are linear portions on the inner surface 218. The measuring system 100 may also include a support structure 180, FIG. 4, that maintains the transmitter 110 and the receiver 130 in a fixed position relative to the inner surface 218 during the measurement procedure as will be described below.

Figure 2:
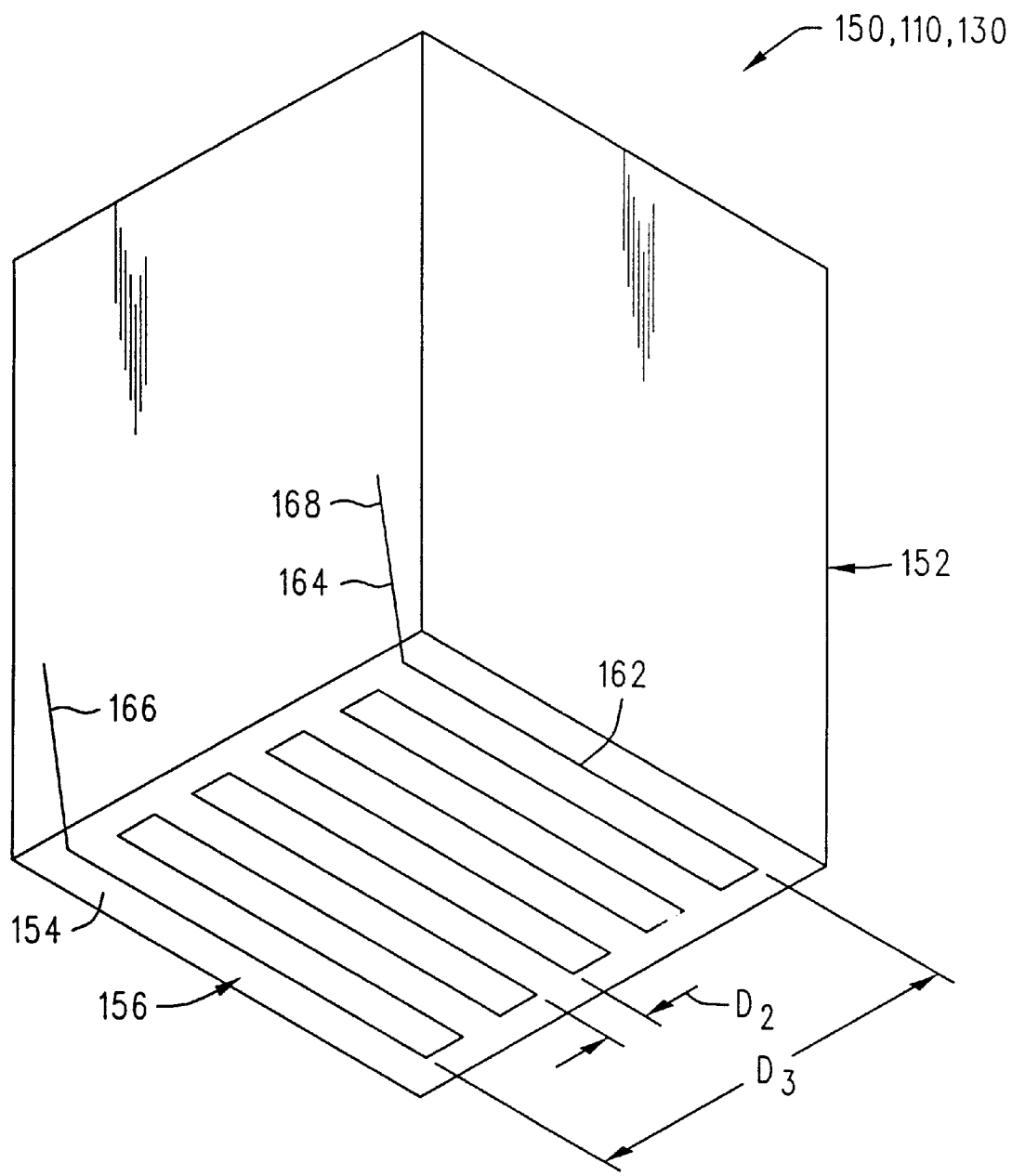
FIG. 2 is bottom perspective view of an electromagnetic acoustic transducer.

The transmitter 110 and receiver 130 are illustrated in greater detail in FIG. 2. The transmitter 110 and receiver 1 30, as described above, are preferably electromagnetic acoustic transducers 150. The EMAT 150 comprises a permanent magnet 152 associated with a meanderline coil 156 (sometimes referred to herein simply as the coil). The magnet 152 has a surface 154, wherein the coil 156 is located adjacent the surface 154. When the measuring system 100, FIG. 1, is in use, the surface 154 is positioned adjacent the inner surface 218 of the coating 216. Accordingly, the surface 154 of the magnet 152 may be appropriately shaped to conform to the contour of the surface being measured, which in FIG. 1, is the curved inner surface 218 of the cylinder 200.

Referring to FIGS. 1 and 2, the coil 156 comprises a conductor 164 having windings 162, a first connector 166 and a second connector 168. Electric current passes through the windings 162 via the first connector 166 and the second connector 168 in a conventional maimer. The conductor 164 in the windings 162 generally forms a winding in a meanderline configuration wherein the windings are spaced apart from each other by a distance D2. In addition, the windings 162 have a length D3. As described below, when the EMAT 150 is used as the transmitter 110, FIG. 1, the distance D2 establishes the wavelength of the surface waves the transmitter 110 induces into the coated material 222. As described below, when the EMAT 150 is used as the receiver 130, the distance D2 establishes the wavelength of the surface waves propagating through the coated material 222 that will induce current to flow through the windings 162.

The EMAT 150 functions as the transmitter 110 by having an electric current pass through the coil 156. The electric current passing through the coil 156 causes a Lorentz force to act on the inner surface 218 of the coating 216 being measured. The Lorentz force in combination with the magnetic field, in turn, causes the inner surface 218 to stress, creating the aforementioned surface waves to propagate through the coated material 222. The surface waves will have a wavelength equal to twice the distance D2 in the windings 162 regardless of their frequency.

The receiver 130 uses the identical EMAT 150 as used in the transmitter 110. Like the transmitter 110, the receiver 130 is positioned adjacent the inner surface 218 of the coating 216 during the measurement process. Unlike the transmitter 110, however, the receiver 130 has current induced into the windings 162 by the propagating surface waves whereas the transmitter 110 passes current through the windings 162 to induce surface waves. When surface waves having a wavelength equal to twice the distance D2 in the windings 162 propagate past the windings 162, the surface waves induce a current in windings 162. The induced current has a waveform that is representative of the surface waves that induced the current. This current and, thus, the waveform, may, as an example, be measured by placing a current measuring device between the first connector 166 and the second connector 168 in a conventional manner.

It is to be understood that the transmitter 110 and the receiver 130 described herein as EMATs 150 are for illustration purposes and that other transducers that induce and receive surface waves of a fixed wavelength into a coated material may be substituted for the EMATs 150. For example, the transmitter 110 may be a piezoelectric device or a heating device, such as a laser. Likewise, the receiver 130 may be a piezoelectric device or a laser acoustic sensor.

Figure 3:
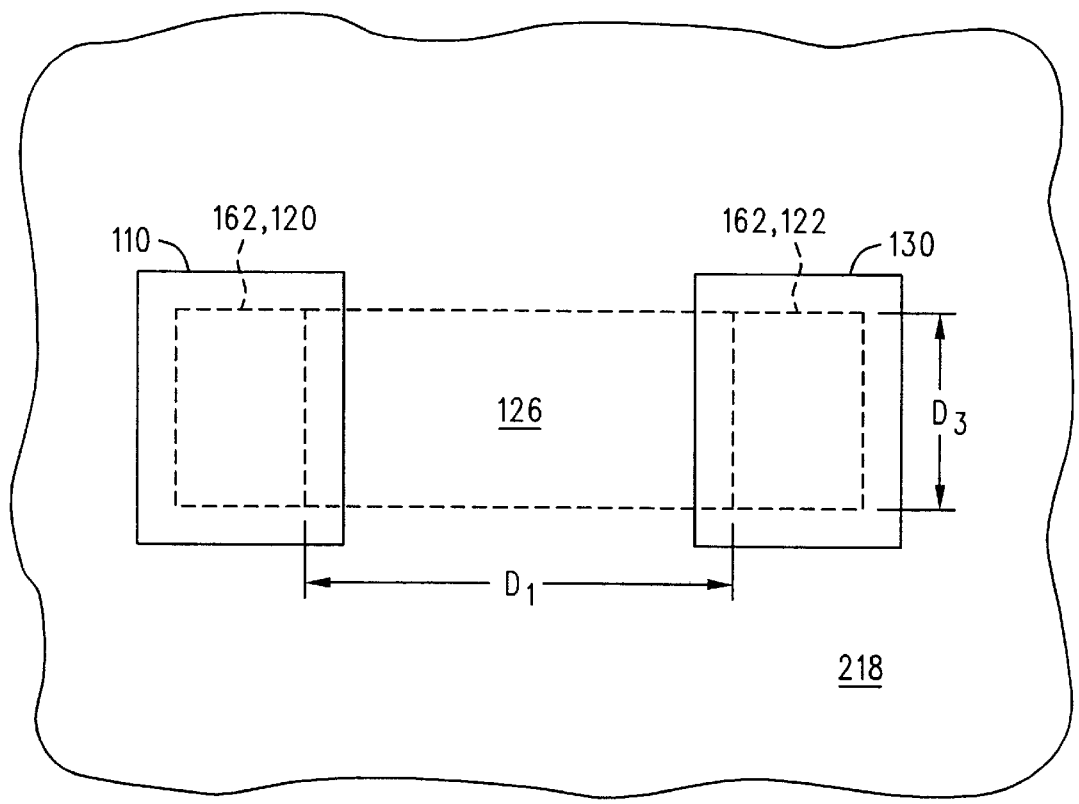
FIG. 3 is a side view of the measurement system of FIG. 1 positioned to measure the thickness of a coating applied to a cylinder wall.

Having described the transmitter 110 and the receiver 130, their association with the cylinder 200 will now be outlined in greater detail. FIG. 3 is a side view of FIG. 1 and illustrates the transmitter 110 and the receiver 130 positioned on the inner surface 218 of the cylinder 200. The windings 162 in the EMAT 150, FIG. 2, of the transmitter 110 and the receiver 130 are illustrated as dashed sections. The transmission point 120 and the receiving point 122 correspond to the windings 162 of the transmitter 110 and the receiver 130 respectively. As was briefly described above and is shown in FIG. 3, the transmission point 120 and the receiving point 122 are linear portions of the inner surface 218. A measuring area 126 exists between the transmitter 110 and the receiver 130. The measuring area 126 has a height that is equal to the lengths D3, FIG. 2, of the windings 162 in the transmitter 110 and the receiver 130. The measuring area 126 has a length that is equal to the distance D1 between the transmitter 110 and the receiver 130. In the non-limiting example illustrated herein, the length D3 is equal to 19 millimeters and the distance D1 is equal to 49 millimeters. Accordingly, the measuring area 126 is equal to 931 square millimeters.

The measuring area 126 represents the portion of the coating 216 that will be measured. The size of the measuring area 126 may be changed by varying the length D3 of the windings 162 or by positioning the transmitter 110 and the receiver 130 at different distances 230 from each other. As will be described in detail below, surface waves are induced into the coated material 222 by the transmitter 110 and propagate through the measuring area 126 to the receiver 130. Because surface waves in a coated material are dispersive, surface waves with a fixed wavelength, like those induced by the transmitter 110, only propagate if the frequency of the waves are within a very narrow band. By transmitting, receiving, and analyzing surface waves with a plurality of frequencies in the coated material 222, the processor 300 is able to determine the frequency of surface waves that propagate through the coated material 222 with minimal attenuation. The phase velocity of these surface waves is calculated and, based on this phase velocity, the thickness T of the coating 216 is readily determined.

Figure 4:
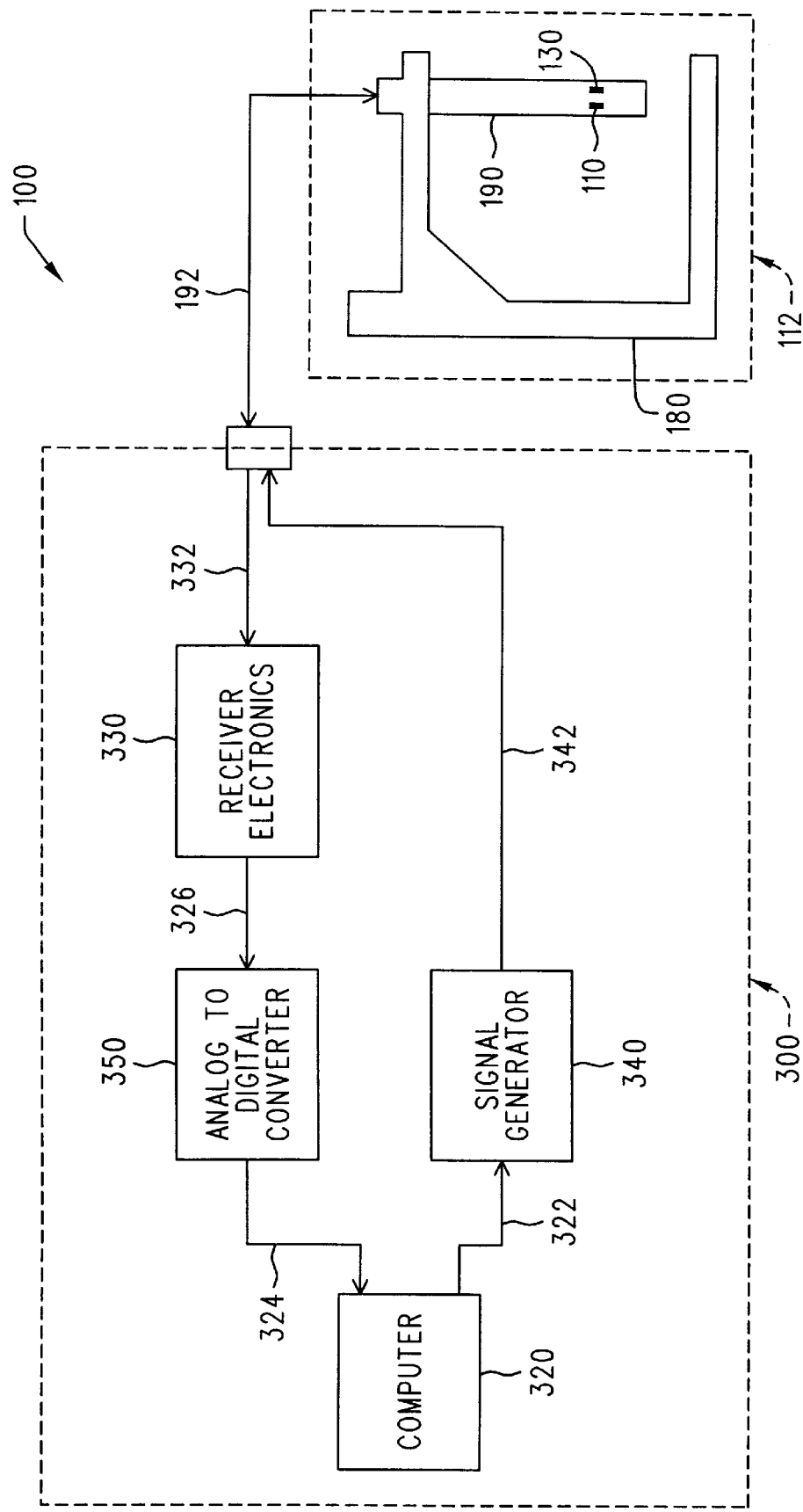
FIG. 4 is a schematic illustration detailing the components employed in the measurement system of FIG. 1.

Having described the transmitter 110 and the receiver 130, the processor 300 will now be described in detail. For illustration purposes, the processor 300 is illustrated in FIG. 1 as being a single unit. The processor 300, however, comprises several components that are illustrated in detail in FIG. 4. Specifically, FIG. 4 is a schematic illustration depicting the interaction between the individual components comprising the measuring system 100. For illustration purposes, the measuring system 100 illustrated in FIG. 4 has been divided into two sections, a transmitter/receiver portion 112 and the processor 300. The transmitter/receiver portion 112 comprises the transmitter 110, the receiver 130, a probe 190, and the support structure 180. The transmitter 110 and receiver 130 are affixed to the probe 190 and the probe 190 is attached to the support structure 180. Wires extending between the transmitter/receiver portion 112 and the processor 300 are bound in a wiring harness 192 and pass through the probe 190. The probe 190 serves to position the transmitter 110 and the receiver 130 in the cylinder 200, FIG. 1. The support structure 180 serves to support the probe 190 while the thickness T, FIG. 1, of the coating 216 on the cylinder 200 is being measured. Accordingly, the support structure 180 may also be appropriately configured to support the probe 190 as the probe 190 is moved to measure the thicknesses of different portions of the coating 216.

The processor 300 includes components that serve to transmit driving frequencies to the transmitter 110 and to receive and analyze waveforms generated by the receiver 130. The processor 300 includes a central processing unit 320 (sometimes referred to herein simply as a "CPU"), receiver electronics 330, a signal generator 340, and an analog to digital converter 350. A receiver line 332 connects the wiring harness 192 and, thus, the transmitter/receiver portion 112 to the receiver electronics 330. A data line 326 electrically connects the analog to digital converter 350 to the receiver electronics 330. A processor line 324 electrically connects the analog to digital converter 350 to the CPU 320. A generator line 322 electrically connects the CPU 320 to the signal generator 340. A transmitter line 342 electrically connects the signal generator 340 to the wiring harness 192 and, thus, to the transmitter/receiver portion 112.

The CPU 320 may be a personal-type computer that has hardware and software which enables the CPU 320 to transmit instructions to and receive data from the other components comprising the processor 300. The receiver electronics 330 amplify, filter, and otherwise condition signals generated by the receiver 130. The analog to digital converter 350 is a conventional analog to digital converter that transforms the signals conditioned by the receiver electronics 330 to a digital format so that they may be processed by the hardware and software in the CPU 320. The signal generator 340 is a signal generator that generates sinusoidal waveforms. The frequencies of these waveforms may, as an example, vary from 1.9 MHz to 2.4 MHz. The signal generator 340 is adapted to receive instructions from the CPU 320 and generate the aforementioned sinusoidal waveforms based on these instructions. For example, the signal generator 340 may output a sine wave of a specified frequency only during a specified period.

The CPU 320 ultimately determines the driving frequencies that are emitted by the transmitter 110 and analyzes the waveforms generated by the receiver 130. This process commences with the CPU 320 determining the driving frequency to be generated by the transmitter 110 and the period associated with this driving frequency. The CPU 320 then transmits instructions regarding the driving frequency to the signal generator 340 via the generator line 322. The signal generator 340 generates the driving frequency per the aforementioned instructions from the CPU 320. The driving frequency is transmitted to the transmitter 110 via the transmitter line 342 and the wiring harness 192. As described below, this driving frequency is induced into the coated material 222, FIG. 1. The CPU 320 then instructs the signal generator 340 to generate other driving frequencies as required to determine the thickness T, FIG. 1, of the coating 216.

Subsequent to the induction of surface waves into the coated material 222 by the transmitter 110, the receiver 130 detects the surface waves and generates an electric signal representative of the detected surface waves. The receiver electronics 330 amplifies, filters, and gates the electric signal. Amplification is required because the signal generated by the receiver 130 is generally too weak to be processed in an accurate manner. Filtering removes noise from the electric signal. Gating the electric signal provides for a specific portion of the electric signal to be processed. For example, leading and trailing portions of the electric signal are typically eliminated from processing. The receiver electronics 330 outputs a conditioned signal to the analog to digital converter 350 via the data line 326. The analog to digital converter 350 then converts the conditioned signal to a digital format and outputs the digital signal to the CPU 320 via the processor line 324. The CPU 320 analyzes the digital signals to determine the frequency of surface waves that propagate in the coated material 222, FIG. 1, with the minimal attenuation. Based on this frequency, the CPU 320 calculates the phase velocity of these surface waves and correlates the phase velocity to a thickness T of the coating 216.

Figure 5:
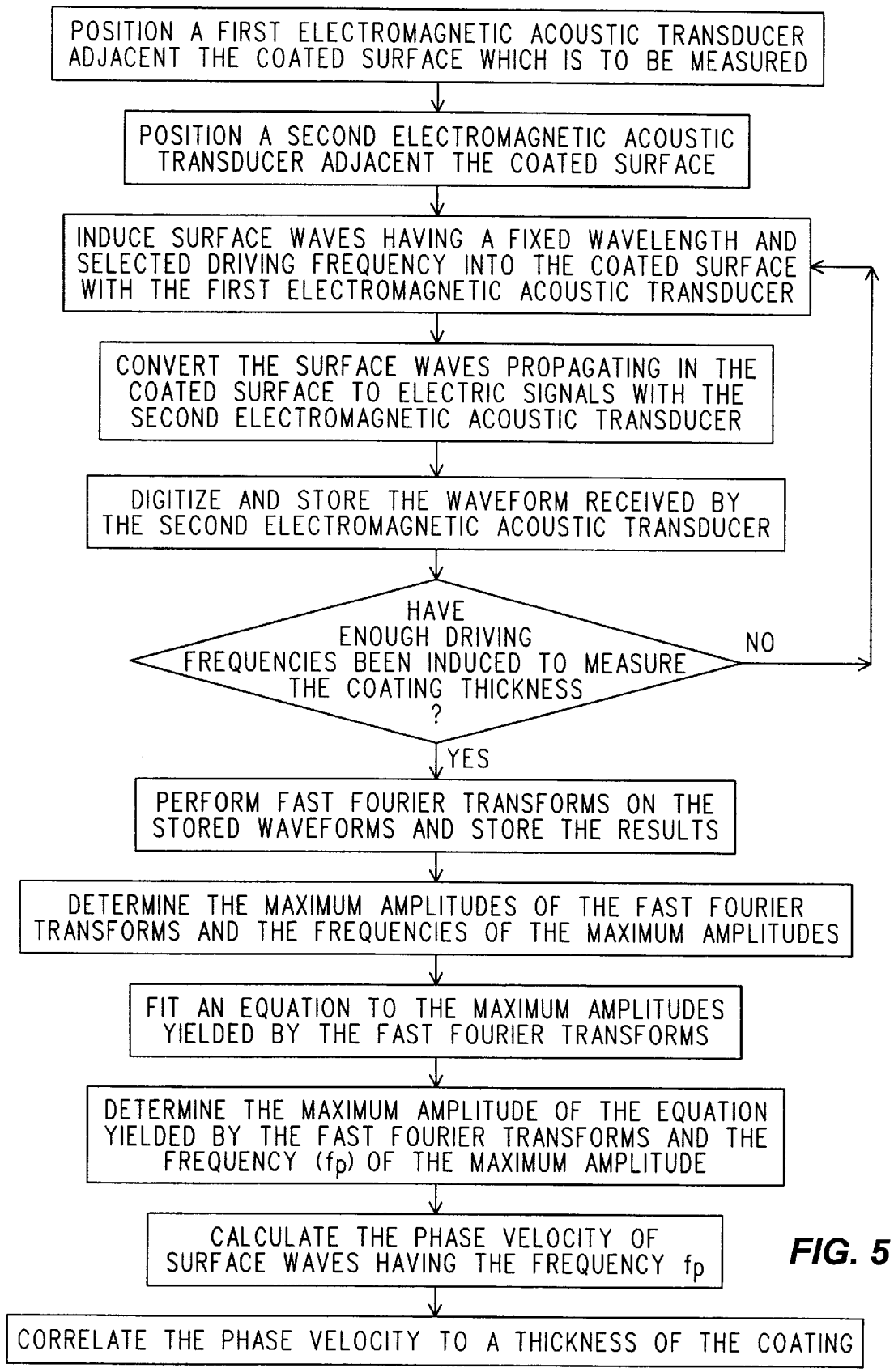
FIG. 5 is a flow chart illustrating a method of using the measurement system of FIG. 1 to measure the thickness of a coating.

Having described the components comprising the measuring system 100, a measurement process which uses the measuring system 100 will now be described with reference to the thickness T of the coating 216, FIG. 1. This measurement process is further illustrated by the flow chart of FIG. 5. It is to be understood that the following description is for illustration purposes only and may be applicable to measuring the thicknesses of other coating materials adhered to other substrates.

Referring to FIGS. 1, 2, and 4, the measuring process commences with the support structure 180 supporting the probe 190 within the cylinder 200. The transmitter 110 attached to the probe 190 is positioned adjacent the inner surface 218 at the transmission point 120. Likewise, the receiver 130 attached to the probe 190 is positioned adjacent the inner surface 218 at the receiving point 122. When the transmitter 110 and the receiver 130 are properly positioned relative to the inner surface 218, the processor 300 commences with the process of measuring the thickness T of the coating 216.

The CPU 320 sends an instruction via the generator line 322 instructing the signal generator 340 to transmit a selected driving frequency to the transmitter 110. Based on this instruction, the signal generator 340 transmits the selected driving frequency to the transmitter 10 via the transmitter line 342 and the wiring harness 192. The transmitter 110, upon receiving the driving frequency, induces acoustic surface waves into the inner surface 218 of the coated material 222. The surface waves are, accordingly, induced at the transmission point 120 and propagate through the coated material 222. It should be noted that waves other than surface waves will propagate in the substrate 210 and the coating 216 when the transmitter 110 induces the surface waves. Only the surface waves propagating in the coated material 222, however, will be used herein to measure the thickness T of the coating 216.

The induction of surface waves into the coated material 222 is repeated for different driving frequencies wherein each driving frequency is coherent and all the driving frequencies have the same wavelength. As described above, the wavelengths of the induced surface waves are fixed by the distance D2 in the windings 162 of the EMAT 150, FIG. 2. The wavelengths of the driving frequencies illustrated herein are fixed at 1.27 millimeters in the present example. It is to be understood, however, that the wavelength of 1.27 millimeters is for illustration purposes and that other wavelengths of the driving frequencies may be used as determined by routine preliminary pilot testing. The driving frequencies used in the example described herein start at 1.9 MHz, stop at 2.4 MHz, and have steps of 0.1 MHz. These driving frequencies are again for illustration purposes only and it is to be understood that they will vary depending on the intended use of the measuring system 100. Each driving frequency is typically emitted as a short burst, sometimes referred to as a "tone burst," having a fixed number of cycles, e.g., 10 cycles. The use of a short burst is preferred because if the transmitter 110 induces surface waves for an extended period, the surface waves received by the receiver 130 may have traveled throughout the cylinder 200. In doing so, they may have reflected from various surfaces and are likely to be noisy or representative of inaccurate data. Interference may also occur at the receiving point 122, which will typically create difficulty processing the data generated by the receiver 130 because the interference will yield inaccurate data. The transmitter 110 induces the surface waves having a fixed wavelength into the coated material 222 by creating a Lorentz force on the inner surface 218 of the coated material 222, which initiates stress waves in the coated material 222. These stress waves cause the surface waves, which are sometimes referred to as Rayleigh or Love waves, to propagate through the coated material 222. The transmitter 110, being an EMAT, induces surface waves into the coated material 222 having a specific wavelength that is dependent on the distance D2, FIG. 2, of the conductor 164 in the windings 162. It is to be understood that the use of an EMAT to induce and receive surface waves is only applicable to conductive materials. Other devices are capable of inducing surface waves with a fixed wavelength in electrically nonconductive as well as conductive materials. Pulsed laser beams, as an example, can be shaped into lines, which, with the correct geometry and correct energy per pulse, can generate waves with a fixed wavelength. Piezoelectric materials can also be formed into lines and can both generate and receive signals at a fixed wavelength.

The coating 216 adhered to the surface 212 of the substrate 210 functions as a narrow band-pass filter with respect to acoustic surface waves. Accordingly, a particular frequency of surface wave, denoted herein as $f_p$, propagates with minimal attenuation through the coated material 222. Thus, surface waves with frequencies that are higher or lower than $f_p$ will attenuate more than surface waves with a frequency of $f_p$. The CPU 320 will determine $f_p$ and, based on $f_p$ and the fixed wavelength, the CPU 320 will determine the phase velocity of surface waves having the frequency $f_p$. The thickness T of the coating 216 will then be readily determined based on the phase velocity.

As described above, the surface waves induced by the transmitter 110 are dispersive. This dispersion means that surface waves with a fixed wavelength, like those induced by the transmitter 110, only propagate if the frequency of the waves are within a very narrow band. The frequency band of the received waveforms is determined by the bandwidth of the transmitted signal convolved with the effective filter function of the coated material 222 between the transmission point 120 and the receiving point 122.

The receiver 130, as was previously described, is an EMAT that is substantially similar to the transmitter 110. The receiver 130 is positioned adjacent the coating 216 at the receiving point 122, which is located at a distance D1 from the transmitter 110. As the surface waves propagate past the receiving point 122, they induce an electric current in the windings 162, FIG. 2, of the conductor 164. The distance D2 of the conductor 164 in the windings 162 of both the receiver 130 and the transmitter 110 are equal, therefore, the receiver 130 will only convert surface waves having the same wavelength as those induced by the transmitter 110 to electric signals. Thus, the distance D2 functions as a filtering mechanism to assure that the surface waves induced by the transmitter 110 are distinguished from other waves that may propagate through the coated material 222. The receiver 130 transmits a time domain representation of the received surface waves to the receiver electronics 330 via the wiring harness 192 and the receiver line 332. For each driving frequency induced into the coated material 222 by the transmitter 110, the receiver 130 transmits an electrical representation of the waveform that propagates past the receiving point 122 to the receiver electronics 330.

As the CPU 320 instructs the signal generator 340 to generate driving frequencies, the CPU 320 simultaneously instructs the receiver electronics 330 that the transmitter 110 is inducing surface waves into the coated material 222. The receiver electronics 330 then monitors the receiver line 332 for a waveform generated by the receiver 130. As described above, the receiver 130 will only generate electric signals of waveforms having frequencies in a narrow band centered about the driving frequency. The receiver electronics 330 gates, amplifies, and otherwise conditions the received waveform and transmits the conditioned waveform to the analog to digital converter 350 via the data line 326. The analog to digital converter 350 transforms the conditioned waveform to a digital format in a conventional manner and transmits the digital signal to the CPU 320 via the processor line 324.

The CPU 320 calculates the fast Fourier transform (FFT) of each received waveform corresponding to each driving frequency induced into the coated material 222 by the transmitter 110. The FFTs yield the frequency spectrums of each received waveform. The CPU 320 then determines the maximum amplitude of each frequency spectrum and the frequency corresponding to each maximum amplitude. Because of the convolution of the transmitted signal frequency bandwidth with the effective band-pass filter of the coated material 222, the frequencies of these maximum amplitudes will not necessarily correspond to the driving frequencies of the induced surface waves. The frequencies corresponding to the maximum amplitudes will, however, be close to, if not centered about, the frequency $f_p$.

The above-described maximum amplitudes and their corresponding frequencies are stored by the CPU 320 for analysis to accurately calculate $f_p$. As was described above, $f_p$ corresponds to the frequency of surface waves that propagate through the coated material 222 with the least attenuation. Accordingly, the frequency, $f_p$, will be used to determine the phase velocity of surface waves propagating through the coated material 222 with minimal attenuation.

The CPU 320 had previously created an array of maximum amplitudes of the frequency spectrums of the received waveforms and their corresponding frequencies for each received waveform. The CPU 320 determines the maximum amplitude of the array along with the frequency corresponding to this maximum amplitude. The frequency corresponding to this maximum amplitude is referenced herein as $f_a$. The CPU 320 fits a quadratic equation to the maximum amplitude and the values corresponding to the frequencies on both sides of $f_a$. This quadratic equation is further analyzed by the CPU 320 to determine the frequency corresponding to the maximum value of the quadratic equation, which is $f_p$. Based on the equation, phase velocity equals frequency multiplied by wavelength, the phase velocity of surface waves having the frequency, $f_p$, is readily determined based on the fixed wavelength of the surface waves.

The phase velocity for the surface waves having a frequency, $f_p$, is correlated to a pre-calculated data table or equation that references surface thicknesses to phase velocity. Accordingly, the thickness T of the coating 216 is readily determined based on the phase velocity. It should be noted that the thickness T of the coating 216 measured by the measuring system 100 is an average of the coating thickness T between the transmitter 110 and the receiver 130. Specifically, the measuring system 100 measures the average thickness T of the coating 216 in the measuring area 126, FIG. 3.

As described above, the coating 218 functions as a band-pass filter for surface waves wherein the pass band is dependent on the thickness T of the coating 216. If the thickness T of the coating 216 varies between the transmission point 120 and the receiving point 122, the coated material 222 will function as a cascade of band-pass filters. This cascade of band-pass filters will attenuate all frequencies of surface waves. Accordingly, if the receiver 130 does not receive surface waves having at least a predetermined amplitude, the measuring system 100 will conclude that the thickness T of the coating 216 between the transmission point 120 and the receiving point 122 is not uniform. Likewise, if a peak corresponding to $f_p$ of all the received waveforms cannot be determined, the measuring system 100 will determine that the thickness T of the coating 216 between the transmission point 120 and the receiving point 122 is not uniform.

Having described the operation of the measuring system 100, a non-limiting example of using the measuring system 100 will now be summarized. In this example, the measuring system 100, FIG. 1, is being used to measure the thickness T of a carbon steel coating 216 applied to the surface 212 of the cylinder 200 of an aluminum engine block. The thickness T of the coating 216 is typically a few mils, however, it may vary from about zero to eight mils. In this example, the thickness T is related to the phase velocity by the equation:

$$\text{thickness} = 49.65 - 17.89 \times (\text{phase velocity})$$

The measurement procedure commences with the probe 190 of the measuring system 100 being placed into the cylinder 200 that is to be tested. The support structure 180 supports the probe 190 and, thus, the transmitter 110 and the receiver 130 in a fixed position relative to the inner surface 218 during the measurement procedure. In addition, the support structure 180 allows the probe 190 to move within the cylinder 200 to measure the thickness of a plurality of portions of the inner surface 218. It should be noted that neither the transmitter 110 nor the receiver 130 necessarily needs to physically contact the inner surface 218.

The transmitter 110 and the receiver 130 are both EMATs as illustrated in FIG. 2. The distance D2 of the conductor 164 in the windings 162 of both the transmitter 110 and the receiver 130 are 0.635 millimeters. Accordingly, the transmitter 110 is adapted to induce surface waves into the coated material 222 at the transmission point 120 wherein the surface waves have a wavelength of 1.27 millimeters. Likewise, the receiver 130 is adapted to generate electric current when surface waves having a wavelength of 1.27 millimeters propagate past the receiving point 122. The lengths D3 of the windings 162 of both the transmitter 110 and the receiver 130 are 19 millimeters. The transmission point 120 is spaced at a distance D1 of 49 millimeters from the receiving point 122. Accordingly, the measuring area 126, FIG. 3, of the inner surface 218 is equal to 931 square millimeters (49 millimeters multiplied by the length D3 of 19 millimeters). As described above, the measuring system 100 measures the average thickness of the coating 216 in the measuring area 126.

When the transmitter 110 and the receiver 130 are properly positioned within the cylinder 200, the CPU 320 instructs the signal generator 340 to drive the transmitter 110 with predetermined driving frequencies. The signal generator 340 generates a series of driving frequencies in the form of tone bursts wherein each burst has a width of 10 cycles. The driving frequencies used in this example start at 1.6 MHz, stop at 2.5 MHz, and step every 0.05 MHz. The CPU 320 simultaneously instructs the analog to digital converter 350 to monitor the receiver electronics 330 to detect conditioned signals output from the receiver electronics 330.

Figure 6A:
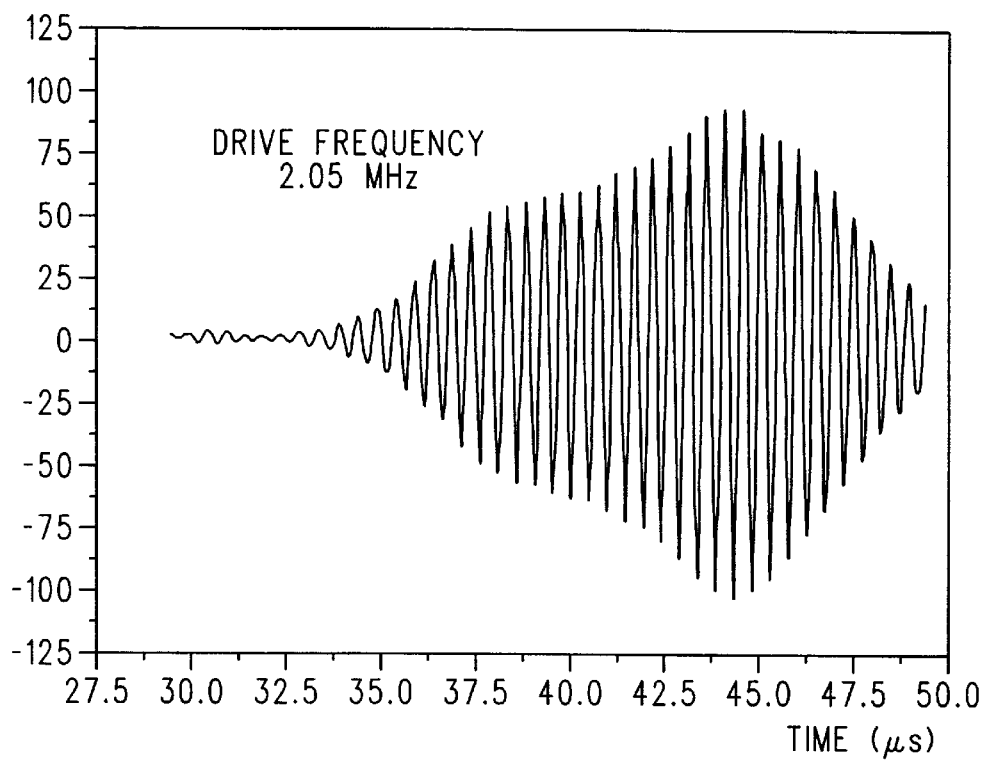
FIGS. 6A–6C are a set of graphs illustrating examples of waveforms received by the acoustic receiver illustrated in FIG. 1.
Figure 6B:
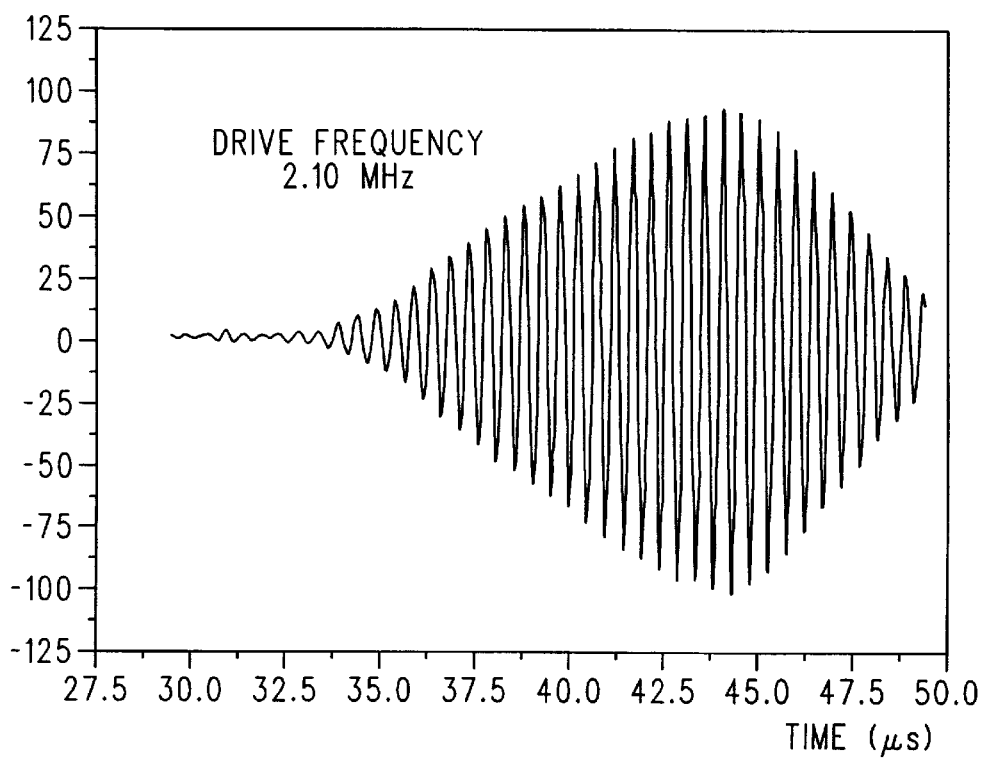
Figure 6C:
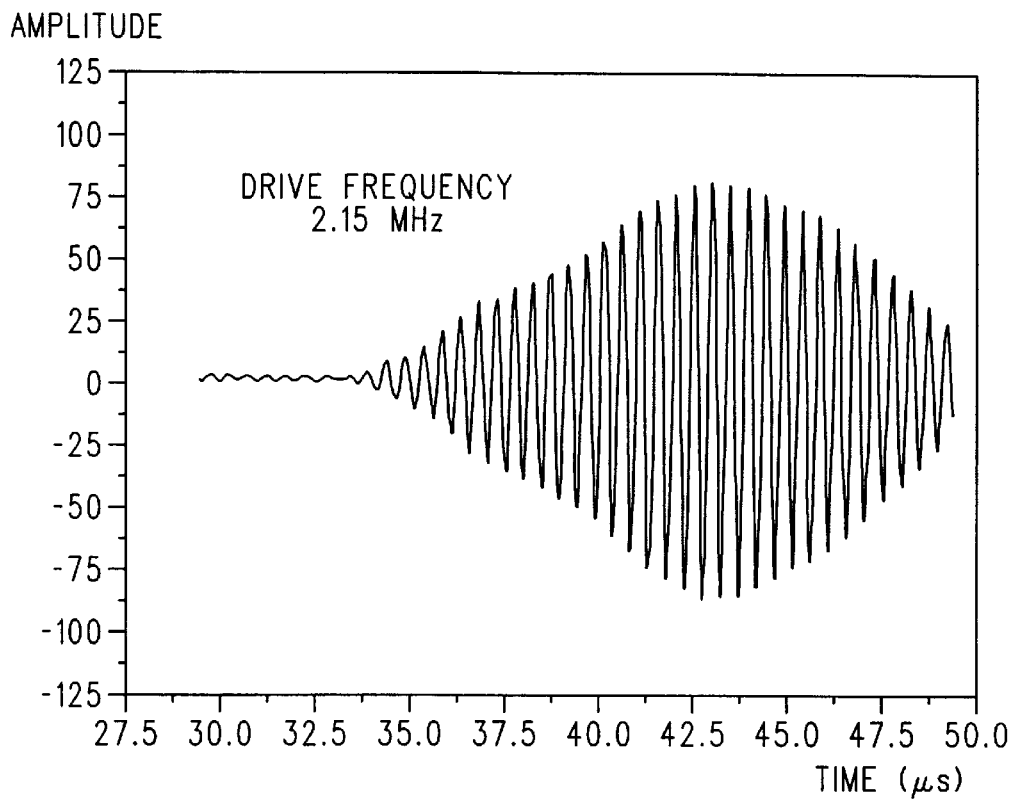

The surface waves generated by the transmitter 110 are dispersive which means that surface waves with a fixed wavelength, like those induced by the transmitter 110, only propagate if the frequency of the waves is within a very narrow band. The wavelengths of these surface waves, however, remain constant at 1.27 millimeters. As the surface waves propagate past the receiving point 122, they induce an electric current in the windings 162 of the conductor 164 in the receiver 130, which is representative of the waveform propagating through the coated material 222 at the receiving point 122. The received waveform is the time-domain representation of the convolution of the frequency band of the transmitted surface waves and the effective filter function of the coated material 222. Examples of these received waveforms are illustrated in FIGS. 6A, 6B, and 6C as time domain functions for driving frequencies of 2.05 MHz, 2.10 MHz, and 2.15 MHz respectively. The electric current induced in the receiver 130 is detected by the receiver electronics 330 where it is amplified, filtered, and otherwise conditioned in a conventional manner and transmitted to the analog to digital converter 350 via the signal data line 326.

Figure 7A:
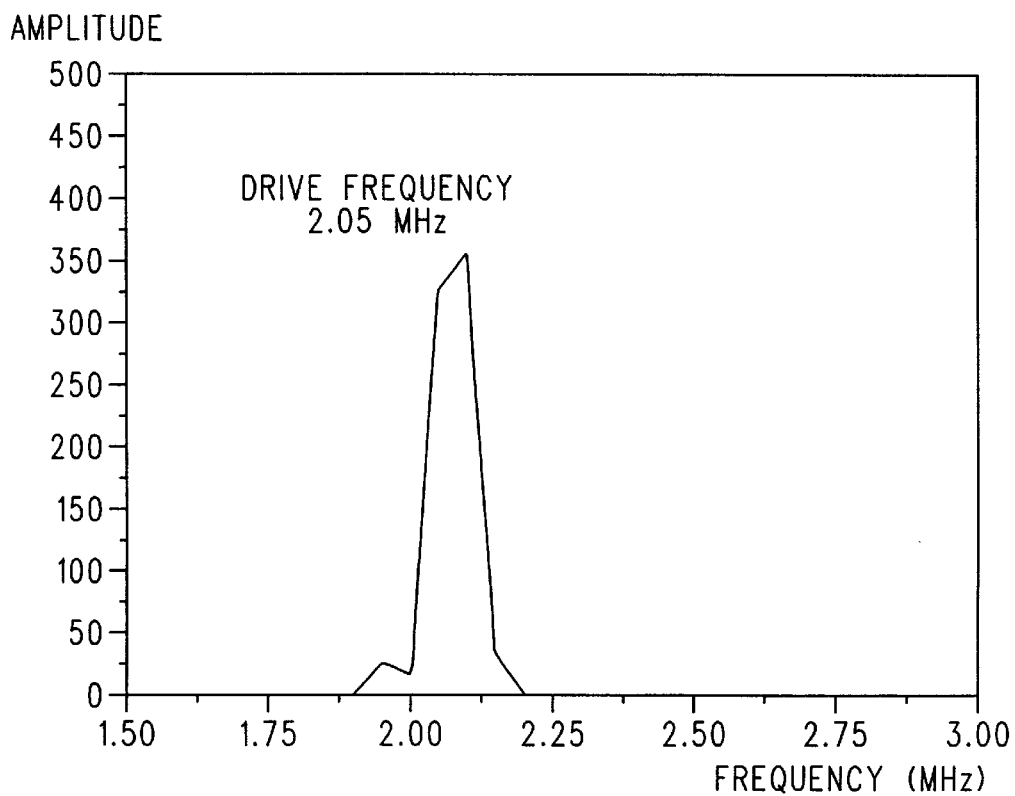
FIGS. 7A–7C are a set of graphs illustrating the frequency spectrums of the waveforms illustrated in FIGS. 6A–6C.
Figure 7B:
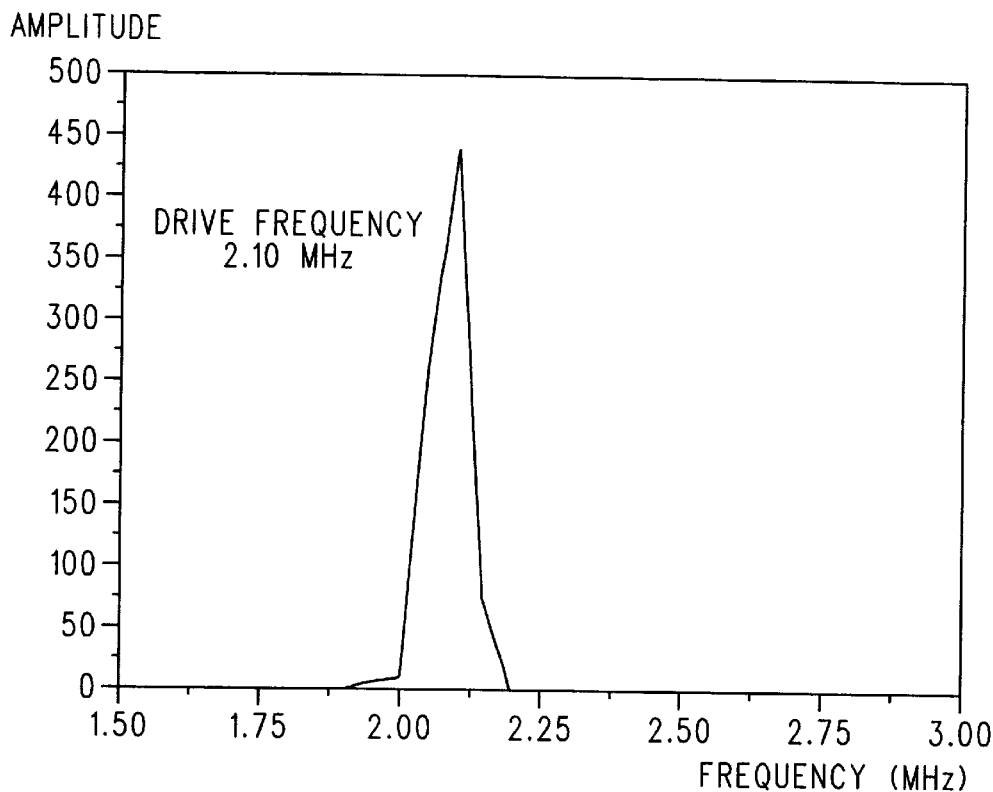
Figure 7C:
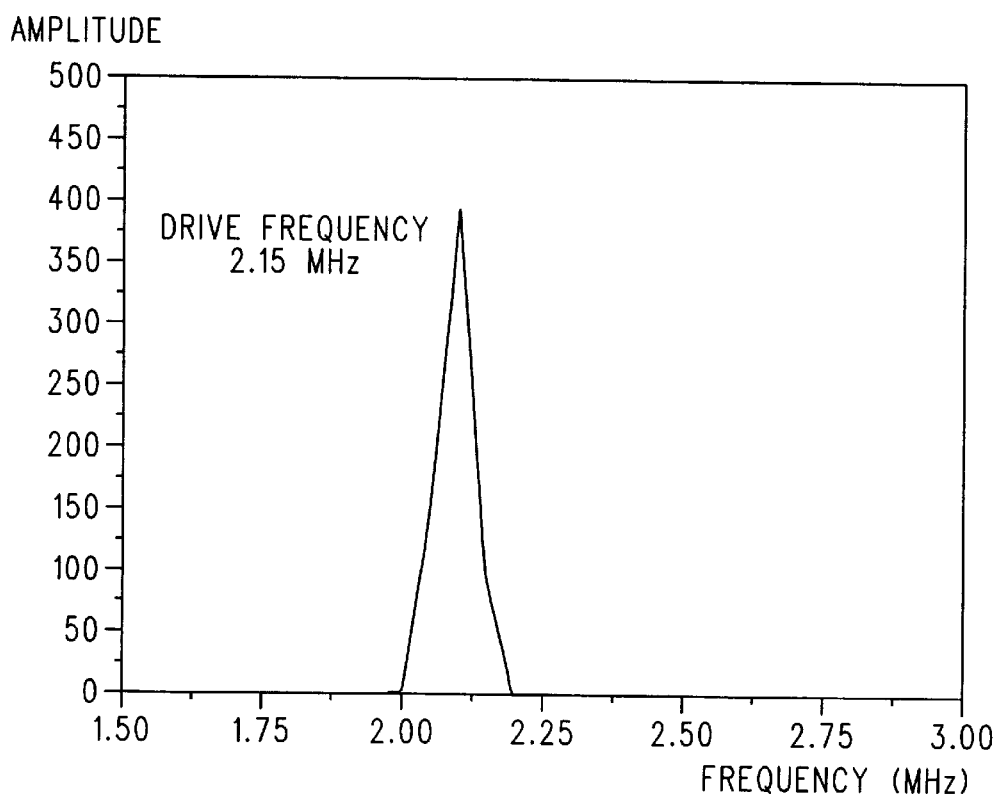

The analog to digital converter 350 converts each waveform transmitted from the receiver electronics 330 to a digital format in a conventional manner. Each digitized waveform is transmitted to the CPU 320 where they are stored by the CPU 320 for future analysis. Each digitized waveform is correlated with the driving frequency induced by the transmitter 110 that created the waveform. The CPU 320 performs an FFT on each stored digitized waveform to yield the frequency spectrum of each waveform. The frequency spectrums for the time domain waveforms of FIGS. 6A, 6B, and 6C are illustrated in FIGS. 7A, 7B, and 7C respectively. As is illustrated in FIGS. 7A–C, the frequencies of the maximum amplitudes of the frequency spectrums do not necessarily correlate to their respective driving frequencies. This is a result of the convolution of the transmitted wave bandwidth and the band-pass filtering of the coated material 222 that propagates surface waves with minimal attenuation at a frequency $f_p$.

Figure 8:
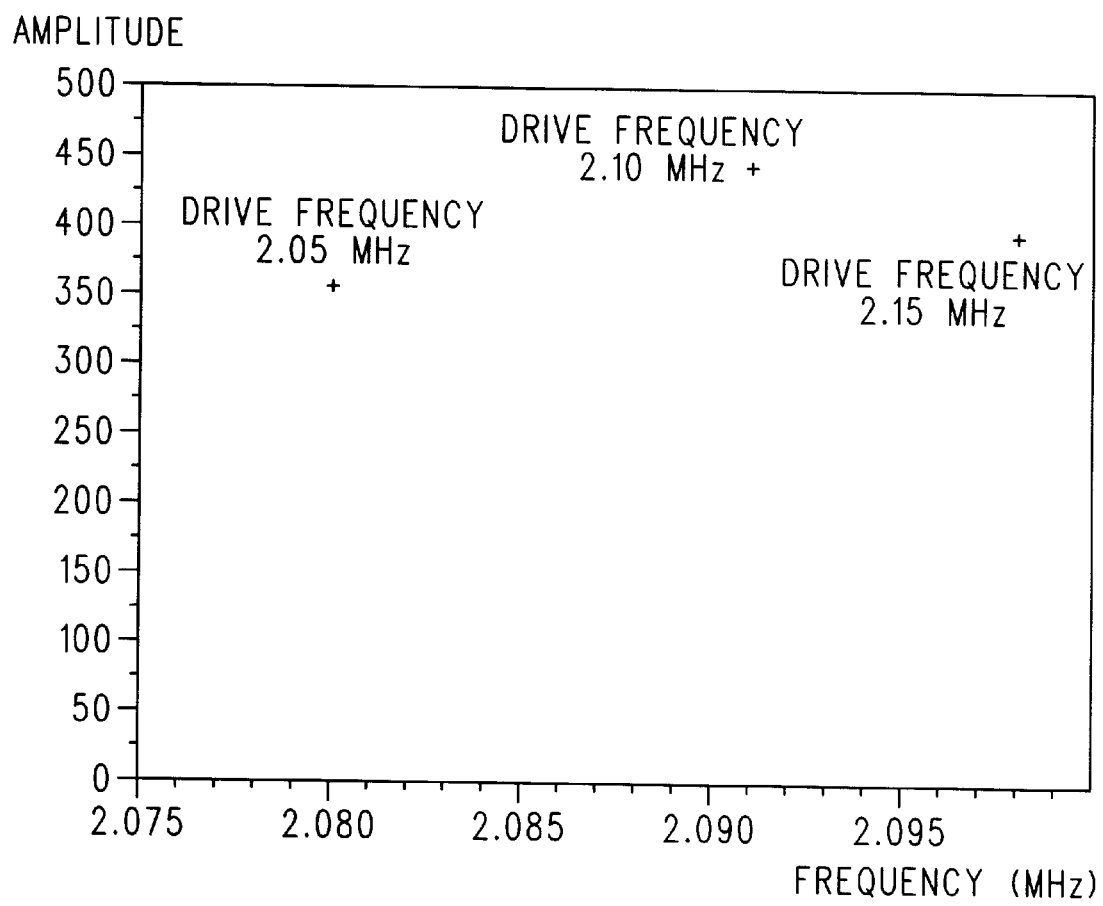
FIG. 8 is a plot of the maximum values of the frequency spectrums of FIGS. 7A–7C versus the frequencies of these maximum values.

At this point, the CPU 320 has data representing the frequency spectrums of all the received waveforms as illustrated in FIGS. 7A–C. The CPU 320 analyzes each frequency spectrum to determine the maximum amplitude of each spectrum and the frequency of the maximum amplitudes. FIG. 8 illustrates a plot of these maximum amplitudes verses the frequencies of these maximum amplitudes for the driving frequencies 2.05 MHz, 2.10 MHz, and 2.15 MHz. Based on these maximum amplitudes illustrated in FIG. 8, the CPU 320 interpolates among the maximum amplitudes to determine $f_p$, which, as described above, is the frequency of surface waves that attenuate minimally as they propagate through the coated material 222. This interpolation is accomplished by fitting a quadratic equation to the maximum amplitudes represented by the plot of FIG. 8. The maximum amplitude of the quadratic equation is then calculated along with its corresponding frequency, which is $f_p$. In the example illustrated herein, $f_p$ has been interpolated to be 2.09 MHz.

As described above, the frequency, $f_p$, is the frequency of surface waves that best propagate through the coated material 222. In other words, surface waves propagating at the frequency, $f_p$, undergo minimal attenuation as they propagate through the coated material 222. Based on a wavelength of 1.27 millimeters and a frequency, $f_p$, of 2.09 MHz, the phase velocity of surface waves are readily calculated to be 2.65 millimeters per microsecond (phase velocity equals frequency multiplied by wavelength). Per application of the above equation, this phase velocity correlates to a thickness T of the coating 216 equal to 2.25 mils. Specifically, the average thickness T of the coating 216 in the measuring area 126 is 2.25 mils.

Having measured the thickness T of the measuring area 126, the transmitter/receiver portion 112 is moved to a different location on the inner surface 218 of the cylinder 200 and the above-described process is repeated. Accordingly, the thickness T of the entire coating 216 may be measured to determine if any portions of the coating 216 are out of specification.

Having described a first embodiment of the measuring system 100, a second embodiment of the measuring system 100 will now be described. The second embodiment uses the same set up of the components comprising the measuring system 100 as was outlined above, however, the measurement procedure is different. The approximate thickness T of the coating 216 is known, so a driving frequency can be selected that undergoes minimal attenuation, but not the minimum attenuation. In this case, the signal generated by the signal generator 340 has a broad bandwidth with significant amplitude over the entire frequency range of interest. The transmitter 110 induces this broadband surface wave into the coated material 222. Only a narrow band of frequencies, however, centered about $f_p$, will be propagated by the coated material 222 and received by the receiver 130. The received signal is processed by the receiver electronics 330 and the analog to digital converter 350. The resulting digitized signal is analyzed by the CPU 320 to determine $f_p$, which as described above, is the frequency that is minimally attenuated as it propagates in the coated material 222. The thickness T is then determined as described above by correlating the phase velocity of the surface wave to a known thickness.

A third embodiment of the measuring system 100 directly measures the velocity of surface waves propagating in the coated material 222. The surface waves are induced by the transmitter 110, and thus, all have a fixed wavelength. The receiver 130 located at a distance D1 from the transmitter 110 receives the surface waves. The processor 300 directly measures the time between the induction of surface waves by the transmitter 110 and the detection of the surface waves by the receiver 130. This time is then divided by the distance D1 to determine the phase velocity of the surface waves. The phase velocity is correlated with a coating thickness T in a conventional manner.

While an illustrative and presently preferred embodiment of the invention has been described in detail herein, it is to be understood that the inventive concepts may be otherwise variously enbodied and employed and that the appended claims are intended to be construed to include such variations except insofar as limited by the prior art.

We claim:

1. A method of determining the thickness of a coating adhered to a substrate, said method comprising:

providing a transmitter and a receiver;

positioning said transmitter at a first position adjacent said coating;

positioning said receiver at a second position adjacent said coating, said first position being spaced apart from said second position;

activating said transmitter to induce at least one surface wave burst into said coating, said surface wave burst comprising a plurality of surface waves, said surface wave propagating in said coating, and said surface waves having frequency spectrum associated therewith;

generating electrical waveforms representative of said surface waves propagating in said coating using said receiver; and analyzing said surface waves to determine the frequency of surface waves within said frequency spectrum that propagate through said coating with minimal attenuation and correlating said frequency to a coating thickness.

2. The method of claim 1 wherein said transmitter is an acoustic transducer.

3. The method of claim 1 wherein said receiver is an acoustic receiver.

4. The method of claim 1 wherein said transmitter is an electromagnetic acoustic transducer.

5. The method of claim 1 wherein said receiver is an electromagnetic acoustic transducer.

6. The method of claim 1 wherein said receiver is a piezoelectric device.

7. The method of claim 1 wherein said activating said transmitter comprises applying an electromagnetic force to said coating.

8. The method of claim 1 wherein said transmitter is a heating device.

9. The method of claim 8 wherein said activating said transmitter comprises heating said coating.

10. The method of claim 1 wherein said receiver comprises a laser.

11. The method of claim 1 wherein said fixed wavelength is about 1.27 millimeters.

12. The method of claim 1 wherein said fixed wavelength is about 0.8 millimeters.

13. The method of claim 1 wherein said substrate is comprised of aluminum.

14. The method of claim 1 wherein said coating is comprised of steel.

15. The method of claim 1 wherein said substrate is a block of an internal combustion engine comprising at least one cylinder bore therein and said coating is adhered to said at least one cylinder bore of said block of said internal combustion engine.

16. The method of claim 1 wherein said analyzing comprises:

analyzing said electrical waveforms representative of said surface waves propagating in said coating to yield the frequency spectrums of said surface waves;

determining the frequency of said surface waves that propagate through said coating with minimal attenuation;

determining the velocity of said surface waves having said frequency; and correlating said velocity to a thickness of said coating.

17. An apparatus for measuring the thickness of a coating adhered to a substrate, said apparatus comprising:

a first transducer for inducing surface waves into said coating, said surface waves having a fixed wavelength and a predetermined frequency;

a second transducer for generating electric data representative of said surface waves; and a processor operatively connected to said second transducer, said processor determining the frequency of said surface waves that propagate in said coating and said substrate with the least attenuation and correlating said frequency to said thickness of said coating.

18. The apparatus of claim 17 wherein said first transducer is an electromagnetic acoustic transducer.

19. The apparatus of claim 17 wherein said second transducer is a piezoelectric device.

20. The apparatus of claim 17 wherein said second transducer is an electromagnetic acoustic transducer.

21. The apparatus of claim 17 wherein said first transducer is a heating device.

22. The apparatus of claim 17 wherein said second transducer comprises a laser acoustic sensor.

23. The apparatus of claim 17 wherein said fixed wavelength is about 1.27 millimeters.

24. The apparatus of claim 17 wherein said fixed wavelength is about 0.8 millimeters.

25. The apparatus of claim 17 wherein said substrate is comprised of aluminum.

26. The apparatus of claim 17 wherein said coating is comprised of steel.

27. The apparatus of claim 17 wherein said substrate is a block of an internal combustion engine comprising at least one cylinder bore therein and said coating is adhered to said at least one cylinder bore of said block of said internal combustion engine.

* * * * *